United States Patent [19]

Clingman, Jr.

[11] 4,125,018

[45] Nov. 14, 1978

[54] METHOD OF AND MEANS FOR ACCURATELY MEASURING THE CALORIFIC VALUE OF COMBUSTIBLE GASES

[75] Inventor: William H. Clingman, Jr., Dallas, Tex.

[73] Assignee: Precision Machine Products, Inc., Dallas, Tex.

[21] Appl. No.: 791,462

[22] Filed: Apr. 27, 1977

Related U.S. Application Data

[63] Continuation-in-part of Ser. No. 682,578, May 3, 1976, Pat. No. 4,032,256.

[51] Int. Cl.$^2$ ............................................. G01N 25/30
[52] U.S. Cl. .............................................. 73/190 CV
[58] Field of Search ................................... 73/190 CV

[56] References Cited

U.S. PATENT DOCUMENTS

| | | | |
|---|---|---|---|
| 3,393,562 | 7/1968 | Breedlove | 73/190 |
| 3,777,562 | 12/1973 | Clingman, Jr. | 73/190 |

*Primary Examiner*—Herbert Goldstein
*Attorney, Agent, or Firm*—Joseph H. Schley; Thomas L. Cantrell

[57] ABSTRACT

Method of and means for accurately measuring the calorific value of combustible gases wherein a mixture of combustible gas and combustion-supporting gas is burned in a pair of flames, the temperatures of the burned gases in both flames being monitored and the volume ratios of the combustion-supporting gas to the combustible gas fed to both burners being adjusted so as to maintain the average of said temperatures at substantially maximum; the volume ratio of said gases which produces said maximum average temperatures varying substantially directly with the calorific value of said combustible gas; the aforesaid calorific value being proportional to said volume ratio of said gases which maximizes said average temperatures; the flow rates of said gases being measured by a single flow sensing system, preferably, of the turbine flowmeter types, or the volumetric flow rate of said combustion-supporting gas being maintained at a constant value while the volumetric flow rate of said combustible gas is being measured; said calorific value measuring method and means being unaffected by ambient temperature and other varying environmental factors. In one embodiment, automatic calibration of the device is obtained by alternately feeding a standard gas and the unknown gas to the burners.

9 Claims, 7 Drawing Figures

METHOD OF AND MEANS FOR ACCURATELY MEASURING THE CALORIFIC VALUE OF COMBUSTIBLE GASES

This application is an improvement of the William H. Clingman, Jr. U.S. Pat. No. 3,777,562, issued Dec. 11, 1973, and is a continuation-in-part of my copending U.S. application entitled IMPROVED METHODS OF AND MEANS FOR ACCURATELY MEASURING THE CALORIFIC VALUE OF COMBUSTIBLE GAS, filed May 3, 1976, Ser. No. 682,578, now U.S. Pat. No. 4,062,236, issued Dec. 13, 1977.

SUMMARY OF THE INVENTION

As used herein, the word "air" or the words "dry air" include any combustion-supporting or oxygen containing gas, and the word "gas" includes any combustible gas or gaseous mixture containing one or more combustible gases.

The basic method of this invention includes the following steps:

(1) combustible gas is mixed with dry air or other combustion-supporting or oxygen-containing gas;

(2) mixture is burned in a pair of flames;

(3) temperatures of these flames or burned gases are monitored;

(4) volume ratio of the gases is adjusted so as to maintain the average of said temperatures at substantially maximum;

(5) said volume ratio of said gases which produces said maximum average temperature is measured and is substantially proportional to the calorific value.

The flow rates of these gases may be measured by a single flow sensing system which is, preferably, of the turbine flowmeter type whereby a measured ratio of said flow rate if obtained and is substantially proportional to the calorific value. Alternately, the volumetric flow rate of the air or combustion-supporting gas may be regulated at a constant value with the volumetric flow rate of the combustible gas being measured.

In accordance with the present invention, the employment of a single flow sensing system is of great advantage. At the pressures and flow rates typically involved in a calorific measuring device, turbine meters have been found to be superior to other types of flowmeters. But because of inevitable manufacturing variances between flowmeters, it is difficult to find a "matched pair" suitable for use together in a single apparatus, thus necessitating complex compensating circuits in the electric signal processing equipment which monitors the flowmeters. When all flow measurements are made with a single flowmeter, as in the present invention, the need for matching flowmeters or compensating for their mismatch is avoided.

The aforesaid measured volume ratio is referred to hereinafter as "critical combustion ratio" and may be defined as that volume ratio of the gases which produces maximum average flame temperatures when said gases are premixed and burned. It has been found that the critical combustion ratio of these gases varies substantially directly with the calorific value of the combustible gas and that a very accurate indication of calorific value can be obtained by measuring said critical combustion ratio.

As set forth in the aforesaid Clingman, Jr. patent, it is well-known that the adiabatic temperature of a flame that is produced by burning a mixture of combustible and combustion-supporting gases is a function only of the initial temperature, pressure and chemical composition of the mixture and that said adiabatic temperature is reached in the combustion zone of the flame only if there are no heat losses from the burning gases. Also, if the ratio of combustion-supporting gas to combustible gas is varied in the initial mixture, the adiabatic flame temperature varies and a critical ratio between the gases exists at which said adiabatic flame temperature is at maximum. If the initial mixture contains less combustion-supporting gas when required to achieve this critical ratio, the adiabatic flame temperature is lower and this is generally due to insufficient oxygen being present to achieve complete combustion whereby less heat is released. In the event that the initial mixture contains combustion-supporting gas in excess of that required to achieve the critical ratio, the adiabatic flame temperature is again lower and is generally due to the necessity of heating such excess. Thus, the critical ratio between the gases is equal to the critical combustion ratio defined hereinbefore.

Objects of the invention include the provision of an improved method of and means for measuring the calorific value of combustible gases which are not dependent upon measuring the amount of heat released in combustion, which utilize a single flow sensing system, preferably, of the turbine flowmeter type, to measure the flow rates of both combustible and combustion-supporting gases or said flow rate of said combustible gas may be so measured while said flow rate of said combustion-supporting gas is maintained at a constant value, which are not affected by the turbine calibration factor of the sensing system, which are relatively simple, which are capable of continuous simple operation, which are not affected by ambient temperature and other varying environmental factors and which are adaptable to automatic calibration.

DESCRIPTION OF A PREFERRED EMBODIMENT

Figure 1:
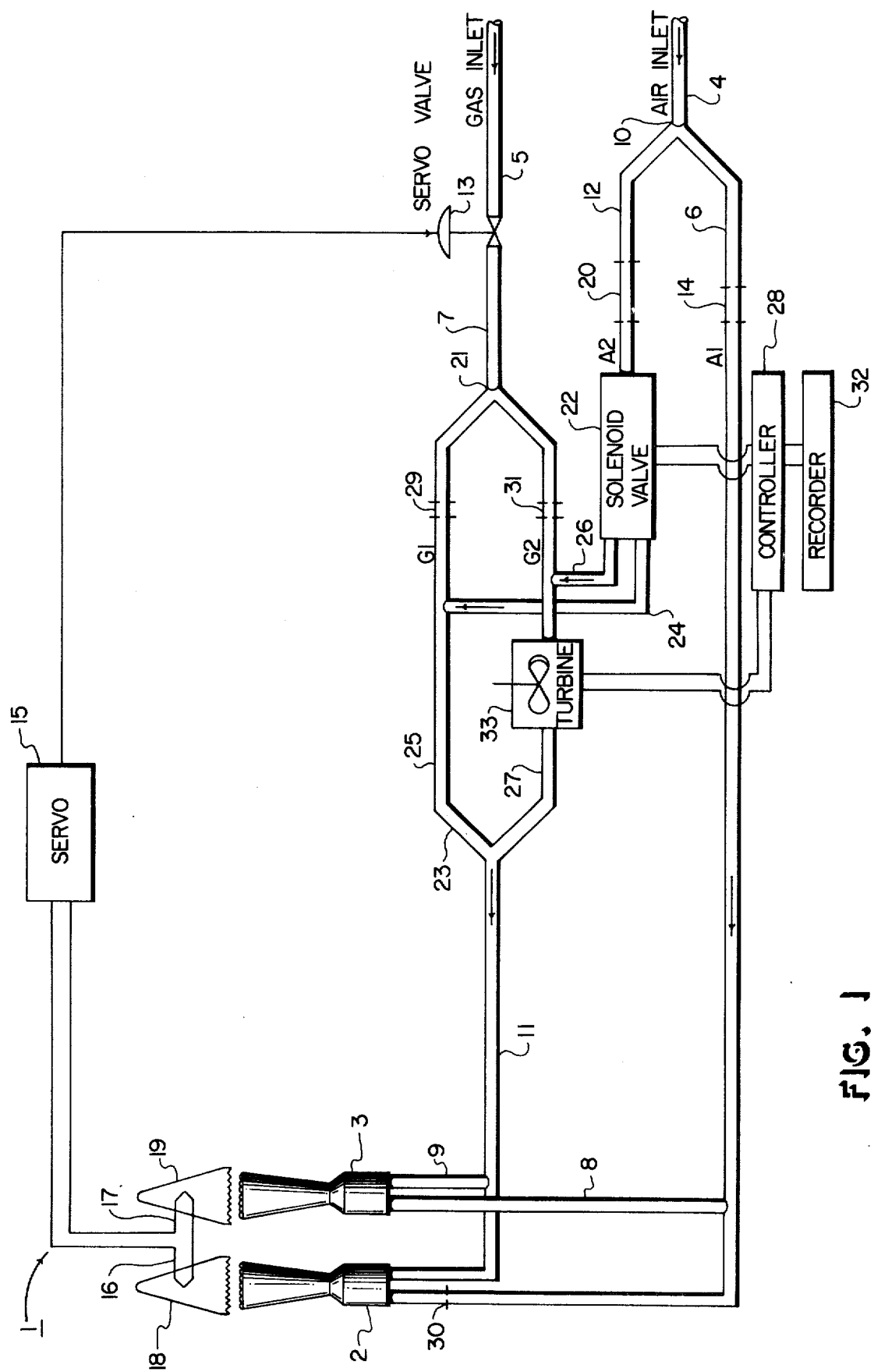
FIG. 1 is a diagrammatic view illustrating an apparatus for carrying out one of the methods of this invention.

In the drawings, the numeral 1 schematically designates an apparatus for accurately measuring the critical combustion ratio or caloric value of a combustible gas which comprises a pair of burners 2, 3 respectively communicating with an air inlet 4 and a combustible gas inlet 5. A fluid conductor or main air line 6 connects the base of the burner 2 to the air inlet 4, and said burner base communicates with the gas inlet 5 through a fluid conductor or main gas line 7. The main air and gas lines 6, 7 are connected to the base of the burner 3 by branch fluid conductors or lines 8, 9, respectively, said gas line 7 having an egress portion 11 of extended length. It is noted that the base of each burner is so constructed that it functions as a mixing chamber for the gas and air conducted thereto by the lines 6, 7, 8, 9. As will be described more fully hereinafter, a forked or Y-shaped fitting 10 is mounted in the ingress portion of the main air line or conductor 6 adjacent and downstream of the air inlet 4.

Figure 7:
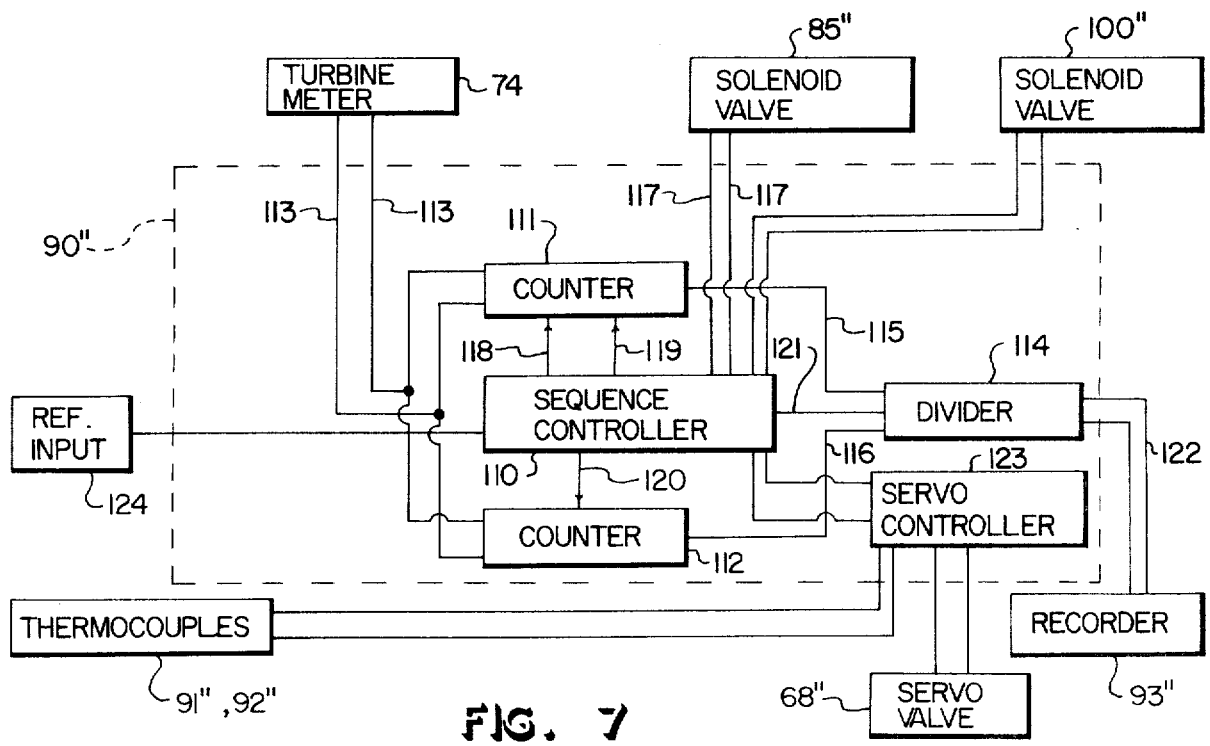
FIG. 7 is a diagrammatic view of the controller of FIG. 6.

A suitable control or servo valve 13 is mounted in the main gas line 7 adjacently downstream of the gas inlet 5 for accurately regulating flow therethrough. This valve is adapted to be actuated electrically by a controller or servo 15 in such manner as to keep at a predetermined value the electrical signal emanating from thermocouples 16, 17 connected in electrical opposition to each other and disposed within carbon monoxide flames 18, 19 of the burners 2, 3, respectively. Reference to FIG. 7 and accompanying description of the Clingman, Jr. patent is made for an illustration of the structure and operation of a suitable controller capable for actuating the gas control valve in accordance with the present invention. As will be apparent, the gas control valve 13 is actuated in such manner that the temperature difference between the burner flames 18, 19 is maintained constant; also, the air to gas ratio is always higher in burner 3 than in burner 2 due to a flow restriction orifice 30 being mounted in the air line 6. Thus, the sign of the temperature difference between the flames depends on whether the ratio of total air flow to total gas flow is richer or leaner than the flow required to maximize the temperatures of said flames. Usually, one of the thermocouples 16, 17 is set at a different position in its flame than the other flame whereby the temperature difference between said thermocouples is a constant plus the temperature difference between the flames.

As set forth in connection with the two burner embodiment (FIG. 3) of the Clingman, Jr. patent, the thermocouple temperature difference is maintained at a value corresponding to substantially maximum average temperatures of the flames by the coaction of the valve 13 and controller 15 which keeps the gas flow in that proportion which maximizes flame temperature.

A pair of forked or Y-shaped fittings 21, 23 are interposed in the main gas line 7 between its egress portion 11 and control valve 13, with the first and second arms of the upstream fitting 21 spaced from and extending downstream toward the respective first and second upstream extending arms of the downstream fitting 23. The respective first arms of the pair of fittings are connected to each other by a branch line or secondary conductor 25, while a parallel line or secondary conductor 27 joins the respective second arms of said fittings. The upstream fitting 21 divides or splits the gas flow evenly between the secondary conductors, and the downstream fitting 23 returns both streams to the egress portion 11 of the main gas line. A flow restriction orifice or capillary tube 29, 31 is mounted in each secondary conductor 25, 27, respectively, so as to maintain the same flow of gas through each conductor. For measuring the flow of gas therethrough, the secondary conductor 27 has a flowmeter 33 of the turbine type connected therein downstream of the capillary tube 31.

The forked or Y-shaped fitting 10 mounted in the large ingress portion of the main line or conductor 6 adjacent and downstream of the air inlet 4 has its arms extending downstream. One of the arms of the fitting 10 forms a part of the main air line, while the other arm communicates with a branch line or secondary conductor 12. A flow restriction orifice or capillary tube 14, 20 is connected in each conductor or line 6, 12 downstream of the Y-shaped fitting for maintaining the flow of air through conductor 12 in constant proportion of the air flow line 6. The ratio between the flow orifices or capillary tubes 14, 20 is such that only approximately 5% to 10% of the total flow of air through the air inlet passes through the secondary conductor 12. A solenoid valve 22 is mounted in the latter, downstream of its capillary tube 20, and has a pair of egress conductors 24, 26 communicating with the secondary conductors 25, 27, respectively, of the main gas line 7 downstream of the respective capillary tubes 29, 21. The solenoid valve 22 is adapted to be actuated by a controller 28, of the sequential or step type, which is electrically connected thereto and to the turbine-type flowmeter as well as to a recorder 32 which may be of the chart type.

As will be more fully described hereinafter, the controller 28 comprises digital electronic circuit for switching the valve 22 between (to and from) two positions, for sensing the spin of the turbine of the flowmeter 33 and, at the end of each measurement cycle, transmits the ratio of air to gas for that cycle to memory. In a complete measurement cycle, the solenoid valve is placed by the controller in a first position adding air from the inlet 4 — through the secondary air conductor 12, capillary tube 20 and egress conductor 24 — to the secondary gas conductor 25. In the first position of the valve 22, the rate of spin of the turbine of the flowmeter is proportional to (G2) the flow of gas through secondary gas conductor 27. After the solenoid valve is switched to its second position by the controller 28, the flowmeter turbine 33 requires about 60 to 90 seconds to commence to spin at a steady rate.

Each time the solenoid valve is switched, starting of the next step is delayed for approximately 90 seconds. Also, approximately 90 seconds after the valve 22 switches to its first position, the controller initiates counting of the revolutions of the flowmeter turbine and, in most instances, the number of counts per revolution equals the number of turbine blades. In any event, the controller 28 measures (N1) the number of counts per second and stores this number in a suitable memory register (not shown). The number (N1) is proportional to (G2) the gas flow through secondary gas conductor 27.

Then, the controller 28 switches the solenoid valve to its second position and waits approximately 90 seconds before commencing the count of turbine revolutions. The controller measures (N2) the number of counts per second, which is proportional to (G2 + A2) the gas flow through secondary gas conductor 27 plus the flow of air through said secondary conductor from secondary air conductor 12 by means of egress conductor 26. Then, the controller produces an output signal to the recorder 32 in proportion to (N2-N1)/(N1), thereby completing the cycle.

Preferably, the pressure drops across the solenoid valve 22, flowmeter turbine 29 and burners 2, 3 at the flow rates required for stable flames are of the order of 1 inch of water or less. The flow orifices or bores of the capillary tubes 14, 20, 29, 31 are of such diameters that the pressure drop thereacross is at least 10 pounds per square inch (10 psi). As a result under these conditions, the flows of fluids through capillary 14 of the main air line 6, through capillary 20 of the secondary air conductor 12 and through capillaries 29, 31 of the secondary gas conductors 25, 27 are substantially constant and independent of the position of the solenoid valve.

Since the gas flow orifices or capillary tubes 29, 31 are of the same size, the flow of gas through each of the conductors 25, 27 is equal whereby G1 equals G2 and whereby G2 is in a constant ratio to the total gas flow. To a first approximation, the flow rates through the air flow orifices or capillary tubes are proportional to the pressure differences thereacross and the pressure differences are the same for both, the upstream and downstream pressures being constant. Thus, the air flow (A2) through the secondary air conductor 12 is in a constant ratio to the total air flow, and the coaction of the servo valve 13 and the controller 15 keeps the ratio of total air to total gas flow in proportion to the calorific value of the gas whereby (N2-N1)/(N1) is proportional to said calorific value.

Figure 2:
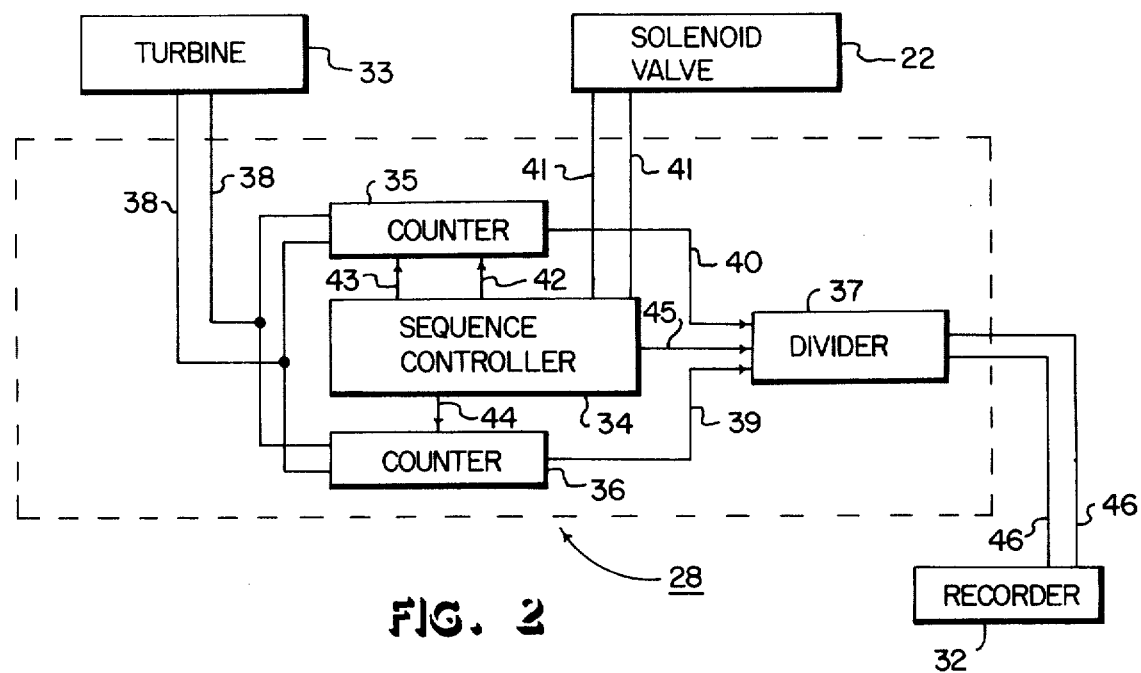
FIG. 2 is a diagrammatic view of the controller of FIG. 1.

As shown in FIG. 2, the controller 28 may comprise a sequence controller 34, a pair of counters 35, 36 connected by a pair of electrical leads 38 to the turbine flowmeter 33 of the secondary gas conductor 27, and a divider 37 connected by electrical leads 39, 40, respectively, to the counters 35, 36. A pair of electrical leads 41 connects the sequence controller 34 to the solenoid valve 22, electrical leads 42, 43 connect the first counter 35 to said sequence controller, and the latter is connected to the second counter 36 by an electrical lead 44 and to the divider 37 by an electrical lead 45. The recorder 32 is connected to the divider by a pair of electrical leads 46. A series of electrical voltage pulses is adapted to be produced by the flowmeter 33 and transmitted by the leads 38 to the first and second counters 35, 36 of the controller 28, the frequency of these pulses being in proportion to the flow of gases through said flowmeter.

The sequence controller 34 is a timing circuit which operates the solenoid valve 22 and the components of the controller 28 in accordance with the aforesaid electrical pulses. At the beginning of each cycle, no power is transmitted by leads 41 to the solenoid valve until after 90 seconds, at which time, the sequence controller activates the first counter 35 by means of a voltage signal transmitted by lead 42. This first counter records each pulse conveyed thereto by leads 38 from turbine flowmeter 33. After approximately 10 seconds, this voltage signal is removed and electrical power is applied to leads 41 so as to activate solenoid valve 22. After 90 seconds, the second counter 36 is activated by a voltage signal through lead 44. Then, the first counter 35 is reactivated in a reverse direction by a voltage signal applied through lead 43. At the end of about another 10 seconds, both counters are deactivated. The number of counts of turbine revolutions remaining on the first counter is then proportional to the air flow (A2) and the number of counts on the second counter is proportional to the gas flow (G2). Next, the lead 45 conducts a voltage pulse or signal from the sequence controller 34 to the divider 37 so as to activate the latter. Voltage pulses conducted through the respective leads 39, 40 from the first and second counters 35, 36 to the divider are in proportion to the number of counts remaining on said respective counters and said divider produces an output signal that is in proportion to said voltage pulses conducted by said leads. This output signal is displayed by the recorder 32 and is in proportion to the calorific value. Then, the cycle of operation is repeated.

In the above description of the method of measurement the roles of combustible gas and combustion supporting gas can be reversed. That is the gas whose calorific value is to be measured can enter at 4 and the air can enter at 5. In this embodiment the calorific value would be in proportion to N1/(N2-N1), which N1 and N2 are determined as described above.

Figure 3:
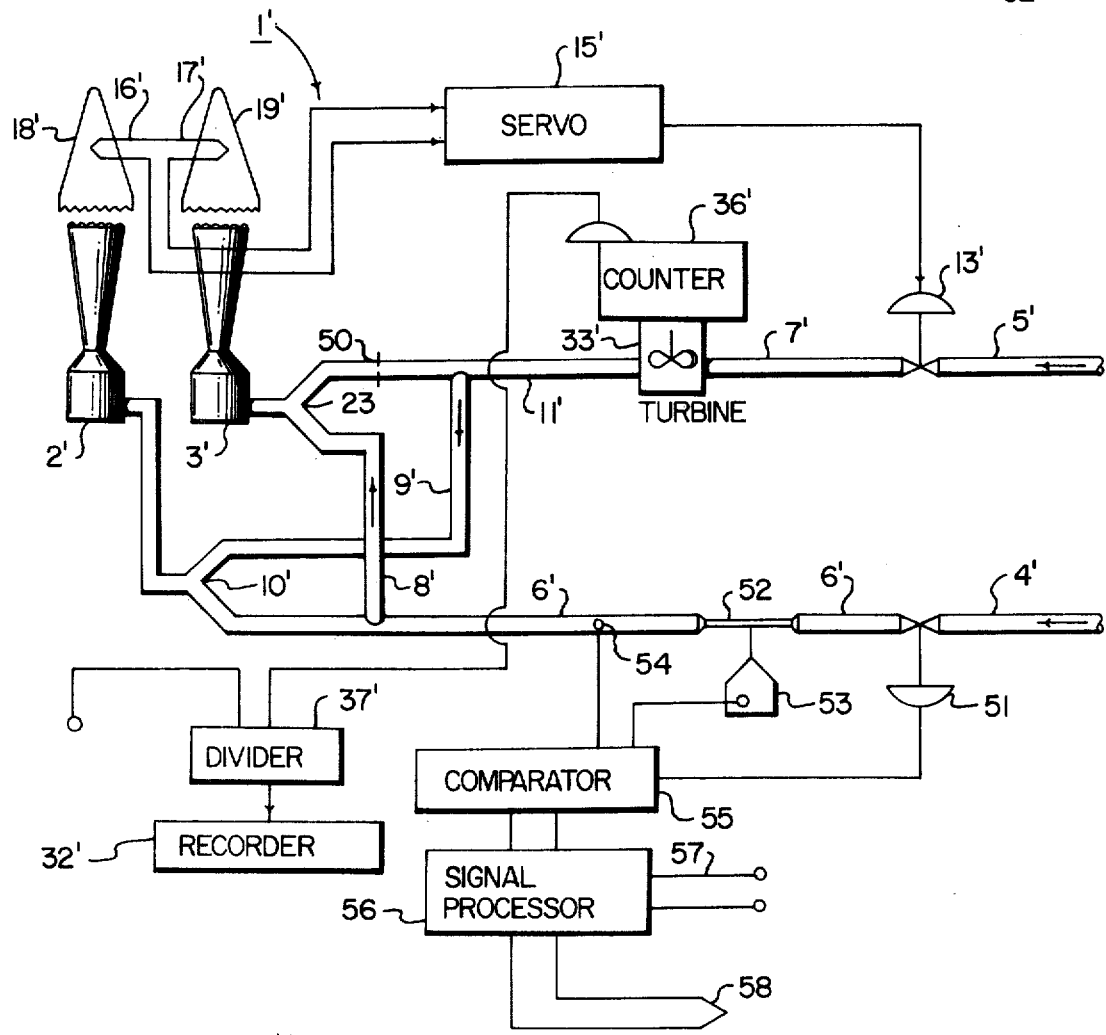
FIG. 3 is a diagrammatic view showing a modified apparatus for carrying out another method of the invention.

FIG. 3 shows an alterate embodiment of the invention; parts corresponding to those in the embodiment of FIG. 1 are given corresponding reference characters with primes (') appended. Like the embodiment of FIG. 1, that of FIG. 3 utilizes only a single flowmeter, preferably a turbine flow meter, and hence provides the same advantage of avoiding the problems of comparing measurements from two meters, each of which has its own mechanical idiosyncracies that affect accuracy of flow measurement.

In the embodiment of FIG. 3 a pair of burners 2', 3', are provided in which fuel-air mixtures are burned in a manner so that the average temperatures of the two flames are maximized, as discussed above. Air is supplied through inlet 4' to main air line 6' which delivers part of the air to the burner 2' through one of the legs of a Y-fitting 10' connected in the main air line. Gas is delivered through inlet 5' to main gas line 7' where its flow rate is measured by turbine flowmeter 33'. Egress portion 11' of the main gas line delivers a portion of the gas through one leg of a Y-fitting 23' to the burner 3' and has a branch line 9' connected to the other leg of the aforesaid Y-fitting 10' for directing the remainder of said gas to the burner 2'. Upstream of the latter fitting, a branch line 8' extends from the main air line 6' to the other leg of the aforesaid Y-fitting 23' for delivering the remainder of the air to the burner 3'. Due to this flow arrangement, separate mixtures of air and gas are provided for separate burning.

The air to gas ratio is burner 2' will always be higher than that in burner 3' by reason of a flow restriction orifice 50 in egress portion 11' in the main gas line.

Gas flow to burners 2', 3' is controlled through the loop consisting of thermocouples 16', 17', located respectively in flames 18', 19', controller or servo 15' and servo operated valve 13', susbstantially in the manner described above in connection with FIG. 1.

In accordance with the invention, the embodiment of FIG. 3 is provided with equipment for regulating the air flow through line 6' so that the volumetric flow rate is constant notwithstanding variations in ambient temperature and pressure, and consequent variations in the temperature and pressure of the air entering inlet 4'. This equipment includes control valve 51 in ingress portion of line 6', capillary 52 in line 6' downstream from valve 51, a pressure sensor 53 positioned to sense the pressure in capillary 52 at a selected point 53a therealong, a pressure sensor 54 downstream from capillary 52, a comparator 55, a signal processor 56, a signal input means 57 to processor 56, and a thermocouple 58, exposed to the ambient air. Signal conducting lines connect the pressure and temperature sensors and the comparator 55 and processor 56. The equipment just identified collectively comprises a constant volume flow regulator.

The regulator delivers air to the burners at a pressure substantially equal to ambient pressure.

The dimensions of capillary 52 are selected so that the air flow through it is laminar, at least from the selected point 53a to the exit end thereof. Selected point 53a is so located that the pressure drop between it and downstream pressure sensor 54 is small compared to the magnitude of the downstream pressure, which is substantially ambient.

The mode of operation of the regulator is as follows: Two inputs (voltages) are delivered to the signal processor 56. One of these is generated by thermocouple 58, and reflects the ambient temperature. The other is an externally supplied constant input (voltage), which may be conveniently provided by a selectably variable voltage source, delivered through means 57. The magnitude of the externally supplied input at 57 determines the flow rate through line 6', and in equations set forth below is designated B.

Signal processor 56 may be a simple analogue computing device of known character that multiplies the externally supplied input by the square root of the absolute temperature (represented by the thermocouple-supplied input) to produce an output or product signal which is delivered to the comparator 55. The output signal of the signal processor thus varies with variations in the ambient temperature. It varies with the externally supplied input only when the latter is deliberately changed for the purpose of changing the volume flow rate in air in line 6'.

Comparator 55, as has been pointed out, receives the output signal of signal processor 56. In accordance with the invention, it also receives pressure signals from pressure sensors 53 and 54. Comparator 55 first creates a pressure differential signal by subtracting signal 54 from signal 53. The so-created pressure differential signal is then compared in comparator 55 with the product signal from the signal processor and an output or central signal is sent from the comparator to control valve 51 for opening or closing it to bring the product signal and the pressure differential signal into equality.

The flow of fluid considerations which underlie this control arrangement for providing an automatically regulated constant volume flow ratio of air are as follows: Because the flow through the capillary 52 is laminar, the volumetric flow rate, F, is given by the following expression:

$$F = \frac{A(P_1^2 - P_o^2)}{U_1 \left(\frac{T_o}{T_1}\right)^{\frac{1}{2}} P_o} \quad (1)$$

where:
$A$ = a constant depending on dimensions of the capillary.
$U_1$ = viscosity of air at temperature $T_1$ in °K.
$T_0$ = ambient temperature in °K.
$T_1$ = a constant (selected) reference temperature in °K.
$P_1$ = pressure at sensor 53 in capillary.
$P_o$ = pressure at sensor 54 downstream of capillary.

Since, as was pointed out above, $(P_1 - P_o)$ is much smaller than $P_o'$ by reason of the selection of points 53 and 54, equation (1) can be rearranged as follows:

$$F = \frac{A(P_1 - P_o)[2P_o + (P_1 - P_o)]}{U_1 \left(\frac{T_o}{T_1}\right)^{\frac{1}{2}} P_o} \quad (2)$$

Furthermore, when $P_1 - P_0 = T_0 \cdot B$, as occurs in the control system as outlined above (B being the selected constant input to signal processor 56), and $(P_1 - P_0)$ is small, equation (2) can be simplified to:

$$F = \frac{2AB}{U_1 \left(\frac{1}{T_1}\right)^{\frac{1}{2}}} \quad (3)$$

all of whose terms are constants. One constant, B, is manually variable, as explained above, and the flow rate F varies directly with it.

In connection with the foregoing development of equations, it should be noted that to a first approximation, the viscosity of air varies with the square root of the temperature and is independent of the pressure, and these facts have been exploited in the control arrangement described above.

Since, in the embodiment of FIG. 3, the volumetric flow rate is constant and controlled, there is no need to measure it in the course of determining the calorific value of the gas. As has been outlined above, the servo 15' automatically adjusts the volumetric flow of gas through valve 13' so that it is in the same proportion to the constant volumetric air flow as the inverse calorific value of the gas. Gas flow alone is measured by turbine 33' and counter 36'. The signal from counter 36' is processed in divider 37' where it is converted to convenient analogue form for driving recorder 32'. The output from divider 37' is in inverse proportion to the signal from counter 36'.

In the apparatus of FIG. 3 the roles of combustion-supporting gas and combustible gas can be reversed provided the combustible gas is always of the same type so as to have the same viscosity. In this case the air would enter conduit 5' and the combustible gas would enter conduit 4'. The output from divider 37' is in proportion to the signal from counter 36'.

Figure 4:
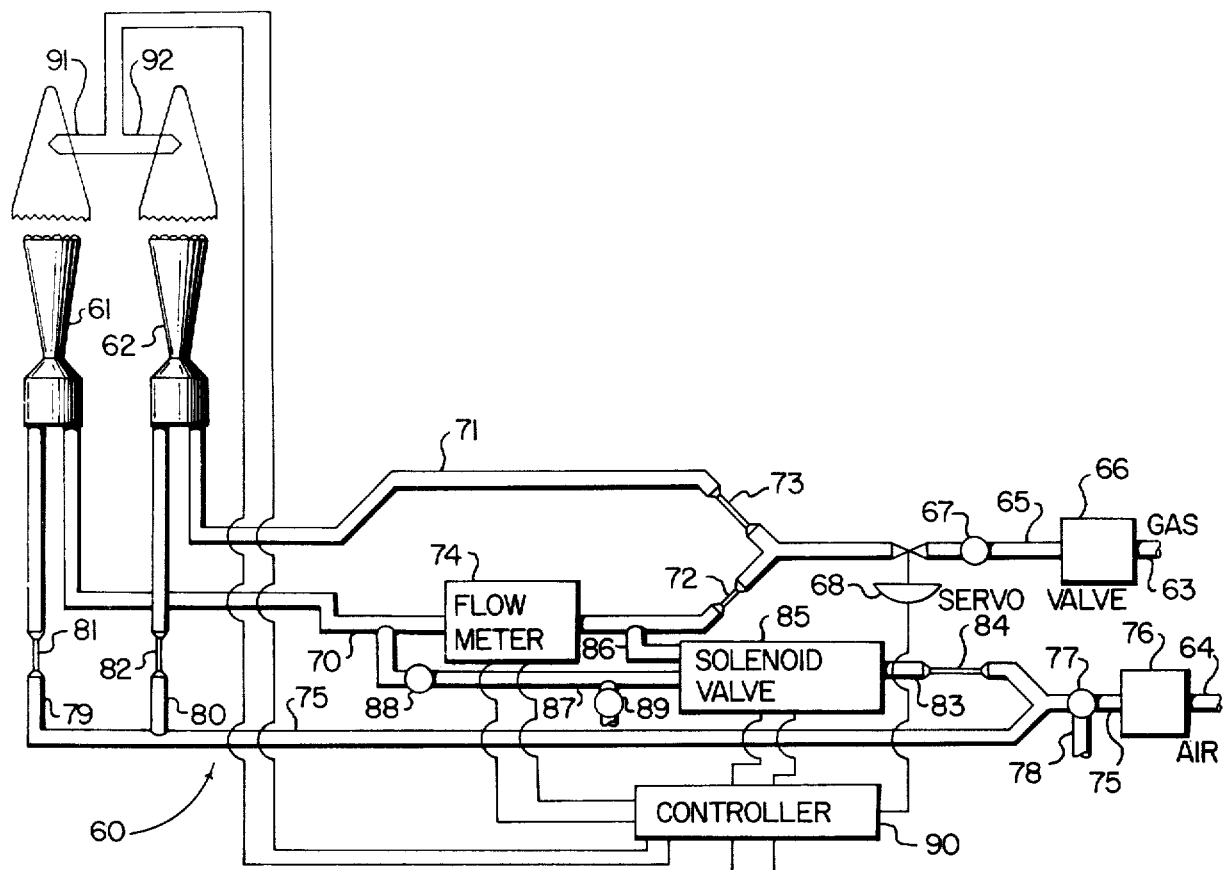
FIGS. 4–6 are diagrammatic views showing other embodiments of the invention.

The embodiment of the invention illustrated in FIG. 4 is capable of operation in two different modes, one of which is essentially the same as that described in connection with FIG. 1 above, and the other of which is quite similar to that described in connection with FIG. 3. In addition, the equipment is arranged to conveniently be placed in two test modes, one of which permits checking on the presence of and character of oscillations in the turbine meter, and the other of which permits checking of the effectiveness of the solenoid operated valve which plays a key role in the operation of the equipment in one mode.

In FIG. 4, the apparatus designated generally as 60 includes a pair of burners 61, 62; a fuel inlet 63; an air inlet 64; various lines, capillaries, valves, etc. described below for delivering fuel and air from the inlets to the burners; and control equipment, also described below.

The fuel delivery system includes a line 65 containing a filter 66, which is preferably of a type adequate to remove particulates down to 0.3 micron, and a pressure regulator 67, preferably of the nonventing type, since it handles flammable gas. Line 65 also contains servo valve 68, which is operated by control equipment discussed below to establish a gas flow which maximizes the average flame temperature in burner 61, 62.

Downstream of servo valve 68, line 65 is split into two branches, line 70 leading to burner 61 and line 71 leading to burner 62. Lines 70 and 71 contain capillaries 72, 73 respectively, which serve to divide the gas flows between lines 70 and 71 in substantially fixed ratio throughout the operating range of the unit. Preferably capillaries 72, 73 are sized with respect to each other so that the flow through line 70 is about twenty percent greater than the flow through line 71. A turbine flow meter 74 is mounted in line 70 where only the fuel gas being delivered to burner 61 passes through it. An advantage of the foregoing arrangement (which is shared by the device of FIG. 1 but not by that of FIG. 3) is that less gas is passed through the turbine in a given period of operation, resulting in less wear on the parts of the meter.

The air delivery means of the apparatus of FIG. 4 includes a line 75 containing filter 76, which, like fuel gas filter 66, is preferably of a type adequate to remove particles down to 0.3 microns. Downstream of filter 75 is a pressure regulator 77, which is preferably of the vented type, which establishes and maintains a substantially constant pressure in line 75 just downstream of regulator 77 by more or less continually venting a small amount of air through vent 78.

At its left hand end, as FIG. 4 is drawn, line 75 is split into two branches, line 79 leading to burner 61 and line 80 leading to burner 62. Lines 79 and 80 contain capillaries 81, 82 respectively, which are equal in dimensions so that the air flows through lines 79 and 80 are equal substantially throughout the operating range of the unit.

Between regulator 77 and the point where line 75 splits into burner lines 79, 80, another branch line 83 is included in the air delivery system. Branch line 83 contains a capillary 84 which is sized with respect to capillaries 81, 82, so that only a small fraction of the air passing through regulator 77 passes through line 83. Branch line 83 terminates in a solenoid valve 85, which has two output lines, 86 and 87. Output line 86 delivers air passing through line 83 and solenoid valve 85 into gas line 70 upstream of turbine flow meter 74.

Output line 87 is provided with a blocking valve 88 and a side vent valve 89. With vent valve 89 closed and blocking valve 88 open, line 87 delivers air from solenoid valve 85 into gas line 70 downstream of turbine meter 74. On the other hand, with the blocking valve closed and the vent valve open, air is vented to the atmosphere through valve 89.

Operation of the apparatus and the processing of flow measurements to yield calorific value data are accomplished through controller 90, whose operation may best be understood from a consideration of FIG. 2 above, and FIG. 7 below, together with their accompanying descriptions. The apparatus associated with controller 90 includes thermocouples 91, 92, positioned in the flames of burners 61, 62, as discussed above, servo valve 68, flow meter 74, solenoid valve 85, and recorder 93.

In one of its operational modes, the apparatus of FIG. 4 flows gas through lines 65, 70, and 71 to burners 61, 62. Air is flowed to the burners through lines 75, 79 and 80. Air is also bled into gas line 70, through branch line 83 and solenoid valve 85. In this mode of operation vent valve 89 is closed and valve 88 is open. The controller 90 cycles solenoid valve 85 so that part of the time air is bled into gas line 70 upstream of turbine meter 74, and part of the time it is bled into line 70 downstream of the meter. Flow meter data is processed under each condition after a time delay to permit the meter to stabilize to the new flow rate.

Since the mixture in burner 61 always has more air in it than the mixture in burner 62, the flame temperatures of the burners will always differ. Thermocouples 91, 92 detect this difference, and act through controller 90 and servo valve 68 to adjust the fuel flow rate to maximize the average flame temperature. The flow meter readings under the alternate air bleed conditions are processed to produce a ratio between air flow and fuel flow, which ratio is proportional to calorific value. The ratio is displayed and recorded on recorder 93.

In its other operational mode the apparatus of FIG. 4 again flows fuel to the burners through lines 65, 70 and 71. The flow rates through lines 70 and 71 differ by reason of the difference in sizes of capillaries 72, 73. In this mode of operation, solenoid valve 85 is maintained by controller 90 in position to feed air into line 87. Blocking valve 88 is closed, and vent valve 89 is open. Hence the air passing through solenoid valve 85 is not fed into gas line 70, but rather is vented through valve 89.

In this mode of operation, air is flowed to the burners through lines 75, 79 and 80. Because of the dimensioning of capillaries 81, 82, the air flow rates to the burners are substantially identical. In addition, the arrangement of regulator 77 (preferably vented) and capillaries 81, 82, has been found to produce an extremely uniform air flow rate. This circumstance is exploited in accordance with the invention to eliminate air flow measurement in the second mode of operation.

In the memory of controller 90, a constant for air flow rate is stored. This value is processed with turbine meter data to produce an air flow to fuel flow ratio which is proportional to calorific value, and which is displayed and recorded. Again, fuel flow rate is continually adjusted to maximize flame temperatures.

The apparatus of FIG. 4 can be arranged into two test modes for trouble-shooting and evaluative purposes. In the first of these, the fuel and air flows are the same as just described in connection with the second operational mode, but the fuel flow rate is held constant by controller 90. This permits oscillations and perturbations of the turbine meter, if any, to be isolated and observed. Any oscillations which occur are not due to variations in fuel flow rate, and must be attributed to, and traced to, other causes, such as mechanical defects.

In the other test mode, vent valve 89 is closed, blocking valve 88 is open, and solenoid valve 85 feeds the bleed airstream into line 87, and thus into fuel line 70 downstream of meter 74. Thus airflow is not measured in this test mode, but the flow rates are otherwise similar to those obtaining in the first operational mode discussed above, assuming that the califoric value of the fuel gas is holding fairly constant. By alternately operating the apparatus in this test mode, and in the first operational mode, and comparing results, one can obtain an indication of how satisfactorily solenoid valve 85 is operating. If the califoric value readings differ significantly between the two modes of operation, then the valve is not switching flow between lines 86 and 87 properly.

Figure 5:
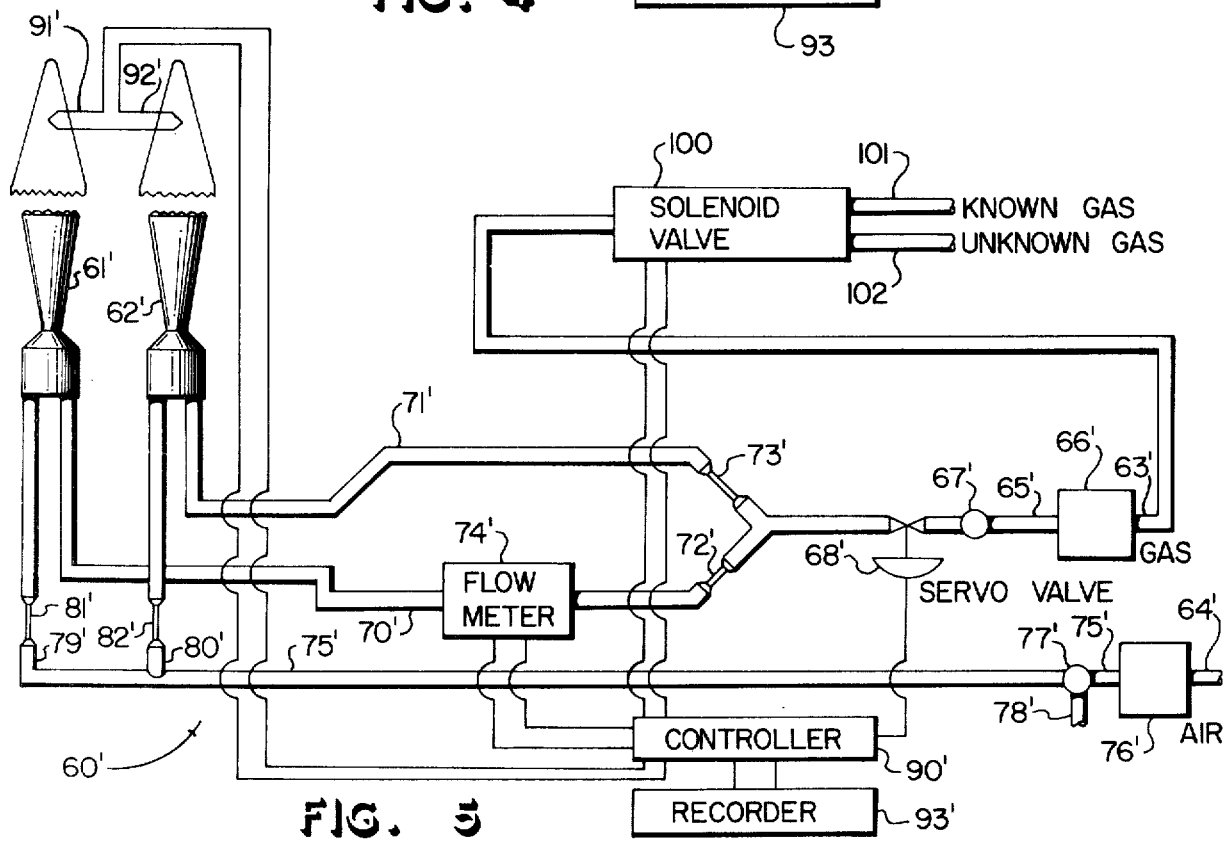

The form of apparatus shown in FIG. 5 is much like that shown in FIG. 4, and the parts which are the same are given the same reference numbers with primes added. Basically, the equipment of FIG. 5 is arranged to operate in the second of the two operational modes discussed above in connection with FIG. 4, that is, with the air flow rate held constant but unmeasured, and with the fuel flow rate varied to maximize flame temperature.

In accordance with the invention, the apparatus of FIG. 5, provision is made to alternately feed the fuel gas of interest (the "unknown gas") and a standard gas of known calorific content (the "knowledge") into fuel line 65 in order to automatically calibrate the system.

Thus, fuel inlet 63' has a solenoid valve 100 at its entrance. Known gas is introduced through line 101, and unknown gas is introduced through line 102. Controller 90' switches solenoid valve 100 periodically to direct first one gas and then the other into fuel inlet line 63.

In operation, air flow to the burners is constant and equal, as discussed above in connection with FIG. 4, second operational mode. Fuel flow is automatically adjusted in response to the thermocouple measurements to maximize flame temperature, no matter which of the gases, known or unknown, is flowing at the time.

One of the electrical factors employed by controller 90' to process turbine meter measurements into a direct indication of calorific value is a proportionally constant (which is preferably stored in the memory of a microprocessor within the controller, but which may be otherwise handled therein in accordance with the state of the art).

The operator of the unit, by manipulation of a dial on controller 90', inserts a value into the unit related to the calorific value of the known gas. This value is used by the sequence controller to adjust the proportionality constant stored within the controller when the known gas is flowing through the unit to a value such that the display at recorder 93' reports a calorific value which is equal to that of the known gas. The value so dialed into the controller is maintained during the next interval of operation, when the unknown gas is flowed through the unit. The proportionality constant may again be adjusted when solenoid 100 next switches known gas into the unit. Simple, quick, and substantially automatic calibration is thus continuously provided in accordance with the invention. Because the equipment of the invention has the characteristic of a fast response time to changes in califoric value, the intervals when the standard or known gas is passed through the unit may be relatively short, thereby minimizing consumption of known gas.

Figure 6:
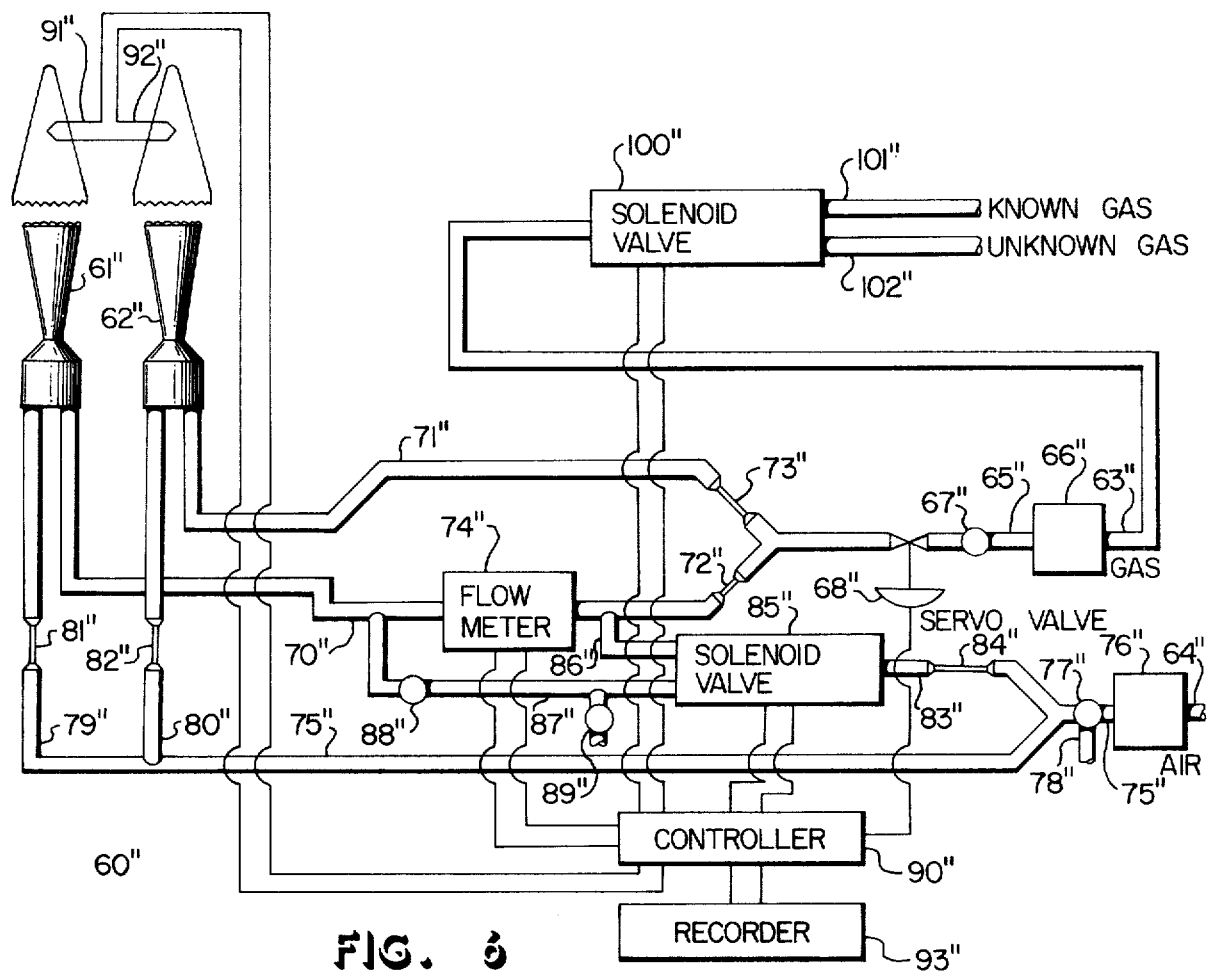

The form of the invention shown in FIG. 6 includes all of the features of FIG. 4, together with the automatic calibration feature of FIG. 5. For this reason corresponding parts are given the same reference characters with double primes. From the discussion above it can be seen that the equipment of FIG. 6 thus has two primary operational modes: one in which part of the air is periodically fed through the turbine meter for measurement purposes; and one in which the air flow is maintained constant but unmeasured. In the later mode, the option is provided for continuous and substantially automatic calibration against a known gas, in accordance with the discussion of FIG. 5. Furthermore, the equipment of FIG. 6 can be switched into the two test modes of FIG. 4 for evaluating turbine oscillations and solenoid valve operation.

FIG. 7 shows in simplified schematic form control equipment forming part of the apparatus of FIG. 6. With suitable simplifications to delete functions not performed, this control equipment may also be used with the units of FIG. 4 or FIG. 5.

The controller 90" may comprise a sequence controller 110, a pair of counters 111, 112, connected by a pair of electrical leads 113 to the turbine flow meter 74" in line 70", and a divider 114 connected by electrical leads 115, 116, respectively, to the counters 111, 112. A pair of electrical leads 117 connects the sequence controller 110 to the solenoid valve 85"; electrical leads 118, 119 connect the first counter 111 to said sequence controller; and the latter is connected to the second counter 112 by an electrical lead 120, and to the divider 114 by an electrical lead 121. The recorder 93" is connected to the divider by a pair of electrical leads 122.

The equipment of FIG. 7 described thus far is substantially the same as the equipment of FIG. 2, and it operates in the manner described in connection with that FIG. to operate the device of FIG. 6 in the mode in which air is periodically bled into line 70" upstream of turbine meter 74".

Controller 90" also includes a servo controller 123 as a part thereof. Its structure and function are substantially the same as the separate servo controller 15 of FIG. 1.

For controlling operations and measurements in the modes of operation in which air flow is held constant but unmeasured, controller 90" has a reference input device 124, which is connected by electrical lead 125 to sequence controller 110. In the modes of operation in which air flow is not measured, counter 112 is not used to record revolutions of turbine meter 74. Instead, a fixed number of counts is stored in counter 112. The number of counts is input to the counter by manually setting a number of reference input device 124, which may be a set of ten-position switches connected in a logic circuit. The sequence controller 110 adjusts counter 112 until the number stored therein is equal to that set on the reference input device 124, which number is a substitute for or equivalent of an actual air flow measurement for use in further processing turbine meter data.

The sequence controller periodically activates counter 111 for a fixed period of time while fuel gas is passing through the turbine meter. Counter 111 counts turbine meter revolutions during each such time interval. The count so obtained is divided into the number stored in counter 112 by divider 114, and the result obtained is displayed and recorded at recorder 93".

During the intervals when counter 111 is not activated, sequence controller 110 activates servo controller 123 so that it can operate servo valve 68" to adjust fuel flow to maximize flame temperature in response to data sensed by the thermocouples The device is manually calibrated in the fixed-but-unmeasured air flow mode of operation by substituting a gas of known calorific value for the gas of interest and manually changing the number input at the reference input device until the value displayed at recorder 93" is that of the known gas.

As explained above, solenoid valve 100" provides for automatic calibration of the unit against a known gas. An input related to the known calorific value of the standard gas is manually set at the reference input device 124. Most of the time the unit operates with unknown gas passing through it. Periodically, however, the sequence controller activates solenoid valve 100" to switch known gas into the unit, and small adjustments can then be made if needed in the number input at the reference input device to maintain the instrument accurately calibrated.

I claim:

1. Apparatus for measuring the calorific value of a combustible gas by mixing it with a combustion supporting gas and burning it, comprising:
   a pair of burners;
   a fuel supply system comprising:
      a main fuel supply line through which all of the combustible gas fed to both burners is passed;

a fuel flow adjusting valve in said main fuel supply line;

a first branch fuel supply line connected between said main fuel supply line at a point downstream of said flow adjusting valve and one of said burners;

a second branch fuel supply line connected between said main fuel supply line at a point downstream of said flow adjusting valve and the other of said burners;

capillary means in each of said branch fuel supply lines for establishing selected rates of fuel flow to said burners; and a turbine meter in one of said branch fuel supply lines; an air supply system comprising:

a main air supply line through which all of the combustion supporting gas fed to both burners is passed;

a pressure regulator in said main air supply line for establishing a substantially constant gas pressure in said line downstream thereof;

a first branch air supply line connected between said main air supply line at a point downstream of said regulator and one of said burners;

a second branch air supply line connected between said main air supply line at a point downstream of said regulator and the other of said burners;

capillary means in each of said branch air supply lines for establishing selected rates of air flow to said burners; thermocouple means for sensing the temperatures of the burned gases in said burners;

means responsive to said thermocouple means for adjusting said fuel flow adjusting valve to establish a fuel flow rate to maximize the average of said temperatures;

means for measuring the revolutions of said turbine meter; and means for deriving a signal uniquely related to calorific value of the combustible gas from said measurement of revolutions.

2. Apparatus in accordance with claim 1 and further comprising:

means for introducing a portion of the gas flowing through the main air supply line into the branch fuel supply line having the turbine meter therein at a point upstream of said turbine meter;

means for periodically effecting said introduction; and means for comparing turbine meter revolutions when both gases are passing through said meter with turbine meter revolutions when only one gas is passing through said meter.

3. Apparatus in accordance with claim 2 in which said introducing means comprise:

a third branch air supply line connected to said main air supply line downstream of said regulator;

a capillary in said third branch air supply line for establishing air flow rate therethrough substantially less than the air flow rate through said first and second branch air supply lines; and a valve downstream of said capillary for alternately introducing air into said second branch fuel supply line upstream and downstream of said turbine meter.

4. Apparatus in accordance with claim 1 in which said signal deriving means includes means for introducing an adjustable calibration factor thereinto, and further comprising means for periodically introducing a combustible gas of known calorific properties into said main fuel supply line so that said calibration factor may be adjusted to produce a signal accurately reflective of the calorific value of said known gas.

5. Apparatus in accordance with claim 4 in which said means for introducing said known gas comprises a valve for alternately blocking flow of unknown gas and initiating flow of known gas and for discontinuing flow of known gas and resuming flow of unknown gas.

6. Apparatus in accordance with claim 1 in which the pressure regulator in said main air supply line is vented.

7. Apparatus in accordance with claim 3 and further comprising means for venting the air passed through said third branch air supply line.

8. Apparatus in accordance with claim 1 in which said turbine meter is located in the branch fuel supply line having the greater gas flow therethrough.

9. A method of determining the calorific content of a combustible gas comprising:

flowing said combustible gas to a pair of burners at selected rates for each burner;

flowing a combustion-supporting gas to said pair of burners at selected rates for each burner;

burning said combustible gas in said combustionsupporting gas in both burners;

sensing the temperatures of the burned gases in both burners;

altering the flow rate of combustible gas to said burners in a direction of maximize the average of said temperatures;

at least part of said combustible gas being continually flowed through a turbine flowmeter upstream of said burners;

measuring the rate of revolution said turbine flowmeter while combustible gas is flowing therethrough;

dividing said measurement into a calibration factor representative of the flow rate of said combustion supporting gas to produce a signal which is a unique function of the calorific content of said combustible gas;

periodically interrupting flow of said combustible gas and substituting therefor a flow of another combustible gas of known calorific content;

adjusting said calibration factor during flow of said known gas to bring the signal produced by said division into correspondence with the calorific content of said gas;

resuming flow of the combustible gas whose calorific content is being determined following said adjustment; and maintaining said calibration factor as adjusted upon said resumption until the next periodic interruption.

* * * * *